United States Patent [19]

Nyiredy et al.

[11] Patent Number: 4,797,215

[45] Date of Patent: Jan. 10, 1989

[54] METHOD FOR SEQUENTIAL CENTRIFUGAL STRATIFICATION CHROMATOGRAPHY FOR SEPARATING COMPONENTS FROM MIXTURES

[75] Inventors: Szabolcs Nyiredy; Clemens Erdelmeier; Otto Sticher, all of Zurich, Switzerland

[73] Assignee: Petazon, Inc., Zug, Switzerland

[21] Appl. No.: 842,703

[22] PCT Filed: Apr. 3, 1985

[86] PCT No.: PCT/CH85/00054

§ 371 Date: Feb. 4, 1986

§ 102(e) Date: Feb. 4, 1986

[87] PCT Pub. No.: WO85/04594

PCT Pub. Date: Oct. 24, 1985

[30] Foreign Application Priority Data

Apr. 5, 1984 [CH] Switzerland .................. 1717/84

[51] Int. Cl.⁴ .................................. B01D 15/08
[52] U.S. Cl. .............................. 210/658; 210/198.3; 210/657
[58] Field of Search .............. 210/198.3, 658, 198.2; 436/162

[56] References Cited

U.S. PATENT DOCUMENTS

| | | | |
|---|---|---|---|
| 2,986,280 | 5/1961 | Magnuson et al. | 210/198.3 |
| 3,229,505 | 1/1966 | Sanford | 210/658 |
| 3,527,350 | 9/1970 | Tuthill | 210/198.2 |
| 3,919,082 | 11/1975 | Falk | 210/198.3 |
| 4,139,458 | 2/1979 | Harrison | 210/657 |
| 4,161,508 | 7/1979 | Janchen | 436/162 |

FOREIGN PATENT DOCUMENTS

3226112 10/1983 Fed. Rep. of Germany .
1262493 2/1972 United Kingdom .

OTHER PUBLICATIONS

Centrifugal Chromatography by Deyl et al., Chromatography Rev., pp. 19–52, 1964.
Sequential Centrifugal Layer Chromatography by Nyiredy et al., 2439 Journal of High Resolution Chromatography, Feb. 8, 1985, pp. 77–79.
Sz. Nyiredy, C. A. J. Erdelmeier and O. Sticher, "Instrumental Preparative Planar Chromatography," in "Planar Chromatography"; ed. R. E. Kaiser; title pages, Table of Contents, and Chap. 5; vol. 1; 1986.

*Primary Examiner*—Ernest G. Therkorn
*Attorney, Agent, or Firm*—Flynn, Thiel, Boutell & Tanis

[57] ABSTRACT

In the new on-line preparative method, and in the inventive apparatus, the addition of flow medium during chromatography can be varied in parallel, locally and temporally. It is thus possible to improve sections of a total chromatogram in their separation by choosing for such partial problems the optimum compositions of the flow medium. The separations are basically obtained in two different ways: (1) Circular separations are carried out with the help of centrifugal force using a sequential technical flow medium supply, wherein the separation occurs from the inside to the outside. The separated substances can be returned through recycling to the inside of the layer. (2) Anticircular separations are carried out with the help of capillary force using a circular solvent supply, wherein the substance zones are concentrated and/or further developed from the outside to the inside. The circular and anticircular possibilities of use can be combined as desired, so that the separation path can be extended practically without limit and thus the capacity and separation performance can be significantly increased.

12 Claims, 6 Drawing Sheets

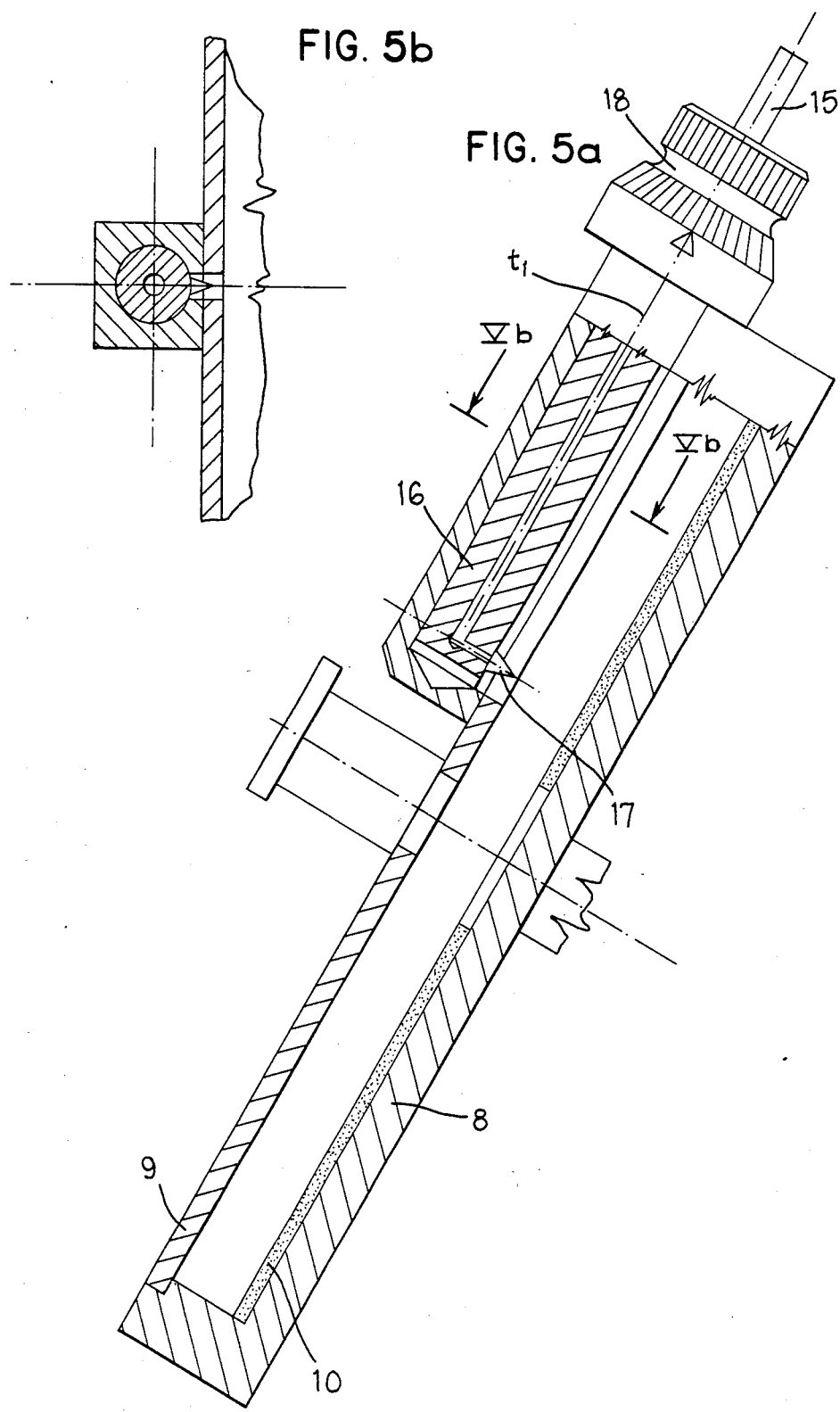

METHOD FOR SEQUENTIAL CENTRIFUGAL STRATIFICATION CHROMATOGRAPHY FOR SEPARATING COMPONENTS FROM MIXTURES

FIELD OF THE INVENTION

This invention relates to centrifugal stratification chromatigraphy and, more specifically, to a method and apparatus for separating components of a mixture utilizing centrifugal stratification chromatography.

BACKGROUND OF THE INVENTION

The use of preparative centrifugal stratification chromatography for separating components of a mixture is known (Z. Deyl, J. Rosmus and M. Pavlicek, Chromatogr. Rev. 6 (1964) 19; E. Heftmann, J. M. Krochta, D. F. Farkas and S. Schwimmer, J. Chromatogr. 66 (1972) 365). This method is suitable for separating natural substances (K. Hostettmann, M. Hostettmann-Kaldas and 0. Sticher, J. Chromatogr. 202 (1980) 154; I. R. Hunter, E. Heftmann, J. Liq. Chromatogr. 6 (1983) 281) and technical or synthetic substances (S. Sekiya, K. Tsuji and M. Yamanaka, Yukagaku 28 (1979) 497; S. Chen and J. Wang, Huaxue Tongbao 10 (1982) 591; F. Derguini, V. Balogh-Nair and K. Nakanishi, Tetrahedron Lett. (1979) (4899).

Difficult separations such as, for example, mixtures with several isomers or complex natural substance mixtures have so far not yet been described in the literature. Certain separation problems can be solved only in several separation steps (C. A. J. Erdelmeier, PH.D. Thesis, ETH Zuerich, No. 2794 (1983).

An apparatus has been known since 1979 (U.S. Pat. No. 4,139,458) which makes possible a centrifugal force which is sufficient for the separations, and also a continuous collection of the separated components, and the manufacture of plates with an all-over constant stratification thickness. The apparatus moreover permits preparative separations on a larger scale (several 100s mg.).

The disadvantage of the present preparative centrifugal stratification chromatography methods and apparatuses is that the capacity and the separation performance, when compared with automatically manufactured thin-layer plates, are generally not sufficient.

The horizontal stratification chromatography makes possible, in contrast to vertical stratification chromatography, a practically linear speed of the eluent, but it does not permit a preparative method of operation without cleaning out of substance zones.

During recent years, a new thin-layer chromatography technique, sequential thin-layer chromatography, has been described as an analytical method (P. Buncak, GIT, Supplement Chromatography (1982) 3; U. Klemm, GIT, Supplement Chromatography (1982) (9). This technique is also based on a horizontal development, that is, it works with a practically linear speed of the eluent.

In the sequential thin-layer chromatography, the flow medium is supplied linearly and the supplying can be varied, in parallel, locally and over time. In this method, the flow medium is conveyed exclusively with the help of the capillary action. It is thus possible to improve stages of a total chromatogram in their separation, by choosing the optimum flow medium composition for these separation problems. However, this method cannot be used for preparative purposes without cleaning out and elution of substance zones.

SUMMARY OF THE INVENTION

The basis for this invention is that the capacity and separation performance of the preparative centrifugal stratification chromatography can be substantially further increased by providing a new sequential technique which utilizes a combination of centrifugal and capillary force while using suitable flow mediums. This new on-line preparative method integrates the advantages of preparative centrifugal stratification chromatography, and analytical horizontal, anticircular and sequential thin-layer chromatography, so that the separation and purification of natural substances or synthetic products is substantially improved.

The present invention broadens the preparative centrifugal stratification chromatographic methods by making it possible to vary the addition of flow mediums, depending on the separation problem, locally and temporally. The flow medium is applied to a point or a ring-shaped zone, but it is always annularly conveyed in the adsorbent layer.

The present invention overcomes the disadvantages of the flow medium supply units of the thus-far known centrifugal stratification chromatography techniques. In this manner, difficult separations are possible using one adsorbent layer. A further goal of the invention is to achieve, by means of a special sequential technique, a separation path which is as large as possible for substances which are chromatographically difficult to separate. Furthermore, it is the subject matter of the invention to split outer zones of mixed substances, which outer zones are formed by chromatographic base separations, using a specific, selective flow medium, so that inner zones, which lie inwardly of the flow medium, remain stationary.

A goal of the invention is to reduce the time of the separation and elution of complex substance mixtures. Finally, it is intended with this invention to quickly elute concentrated and already cleanly separated components with a strong eluent.

BRIEF DESCRIPTION OF THE DRAWINGS

FIG. 3b is a fragmentary sectional view taken along the line IIIb—IIIb in FIG. 3a;

FIG. 4b is a fragmentary elevational side view of the apparatus of FIG. 4a;

FIG. 5a is a fragmentary sectional side view of yet another alternative embodiment of the apparatus of FIG. 1;

FIG. 5b is a fragmentary sectional view taken along the line Vb—Vb in FIG. 5a.

DETAILED DESCRIPTION

Figure 1:
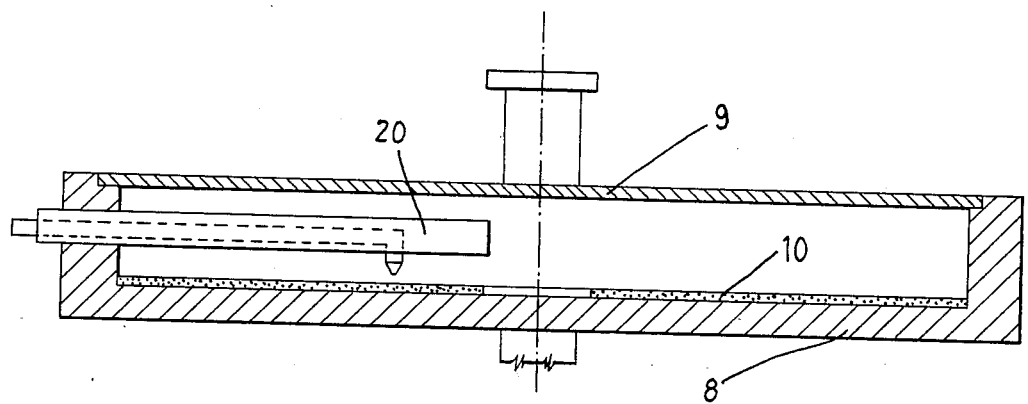
FIG. 1 is a fragmentary sectional side view of a first apparatus which embodies features of the present invention and can be utilized to carry out the inventive method.

Description of the Sequential Technical Flow Medium Supply Units

The method proceeds in various ways (see below) following a first chromatographic base separation.

Four different technical units can basically be used for the operation of the sequential centrifugal stratification chromatography. Of these, the first three units (I) (20 in FIG. 1) work with a rotating rotor, whereby the fluid medium supply unit is fastened either within the chamber or outside thereof above the chamber lid. The fourth, circular fluid medium addition unit (II) (19 in FIG. 2) is placed at a stationary rotor on the plate. Reference numeral 8 in FIGS. 1-5 is the chromatographic chamber, reference numeral 9 is the glass cover with holder, and reference numeral 10 is the chromatographic plate.

Figure 3A:
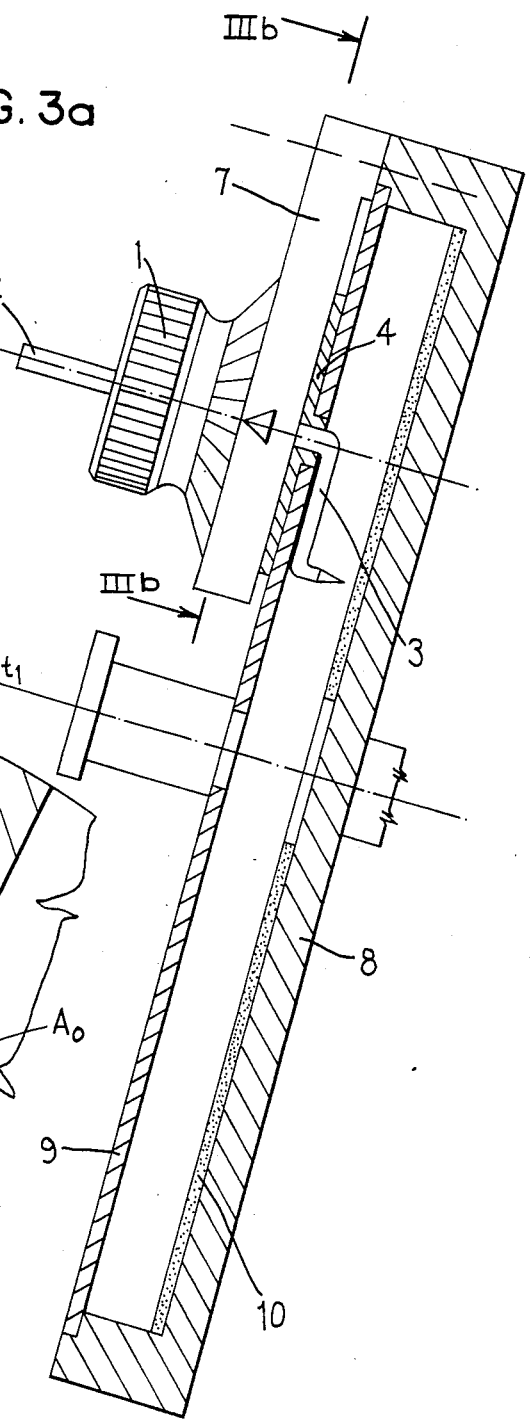
FIG. 3a is a fragmentary sectional side view of an alternative embodiment of the apparatus of FIG.1.
Figure 3B:
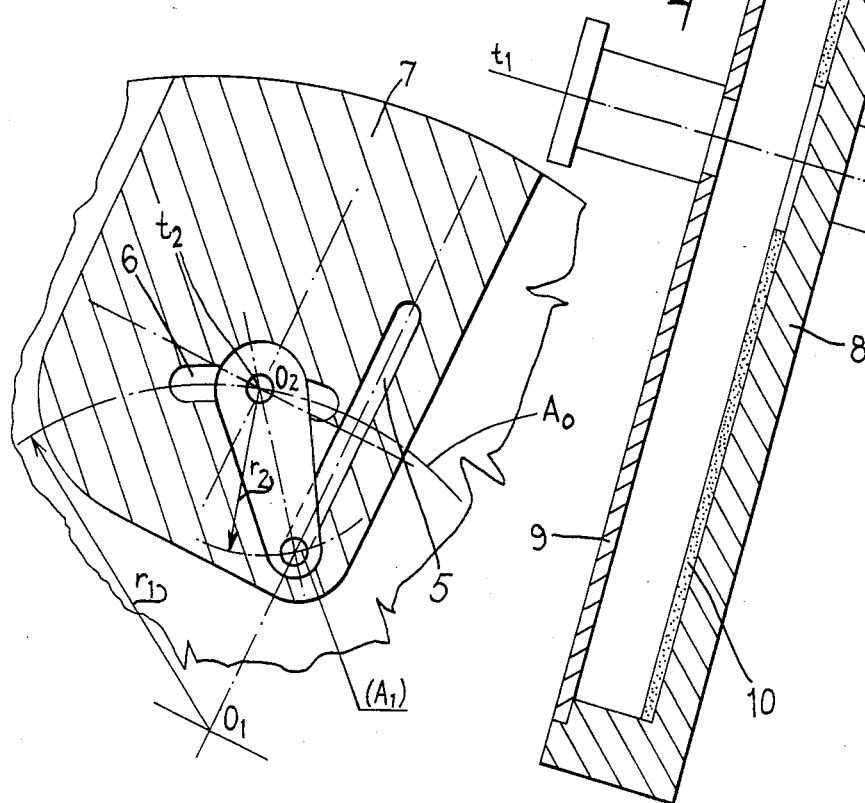

1. The analog place of operation selector having a hinge bracket mechanism (FIG. 3)

The selection of the place of operation is carried out with the adjusting head 1, which has a scale which permits the operation to be reproduced. The addition of the fluid medium is carried out by a glass tube 2 having an axis $t_2$ and a hinge bracket 3. During the selection of the place of operation, the axis $t_2$ of the fluid medium adding unit moves around point $O_1$ on a path of radius $r_1$ in an arc $A_0$, while the axis of the injector moves around the point $O_2$ on a path of instantaneous radius $r_2$ in an arc $A_1$. The structure that provides this freedom of movement of the hinge bracket 3 is shown with reference numerals 5 and 6 in FIG. 3. The base, which is identified with reference numeral 7, is stationary so that the effective path of the arc and thus also the line of movement of the flow medium adding unit is straight. Thus, the injector with the axis point $A_1$ moves along a straight line, while the adjusting head moves on a radius $r_1$ about $O_1$ and also around its own centerpoint $O_2$. Reference numeral 4 designates the seal of the hinge arm in FIG. 3.

Figure 4A:
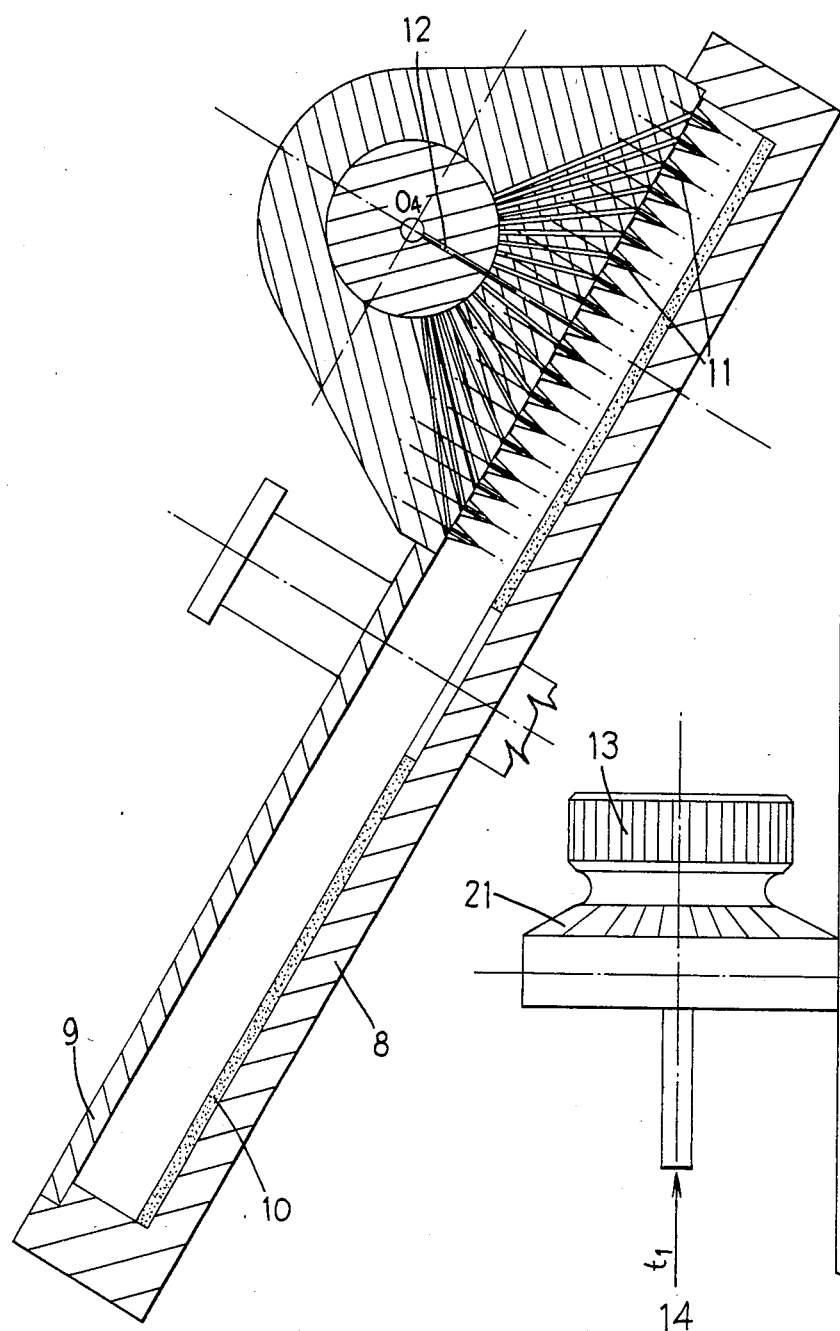
FIG. 4a is a fragmentary sectional side view of a further alternative embodiment of the apparatus of FIG. 1.
Figure 4B:
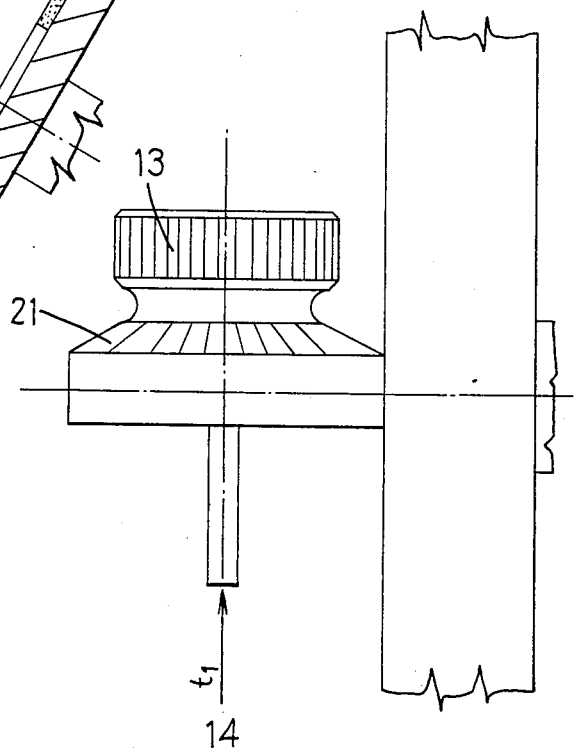

2. The discrete place of operation selector (FIG. 4)

Injectors 11 are provided in the system for the addition of a flow medium, the number of injectors 11 corresponding with the number of places for the addition of flow medium. Each injector 11 communicates with a channel extending from the radial location of such place of operation selector 11 to a place of operation selector cylinder 12. A single radial bore is provided in the cylinder and extends, in dependency on the position of the adjusting head 13 with which the place of operation is selected, from a point $O_1$. The addition of solvent is carried out through a glass tube 14, the axis $t_1$ of which corresponds with the axis of the adjusting head which has a scale 13 thereon.

3. The analog piston unit (FIG. 5)

The pipe 15 for the addition of flow medium with the axis $t_1$ is fitted into a piston 16 which is provided with an outer thread. The instantaneous position of the place of operation 17 depends on the position of the adjusting head 18 having a scale. The adjustment is continuous.

In the technical units which are described above in the paragraphs numbered 1-3, it is possible, by using two or more units for the addition of a flow medium, to add the flow medium at two or more points simultaneously.

Figure 2:
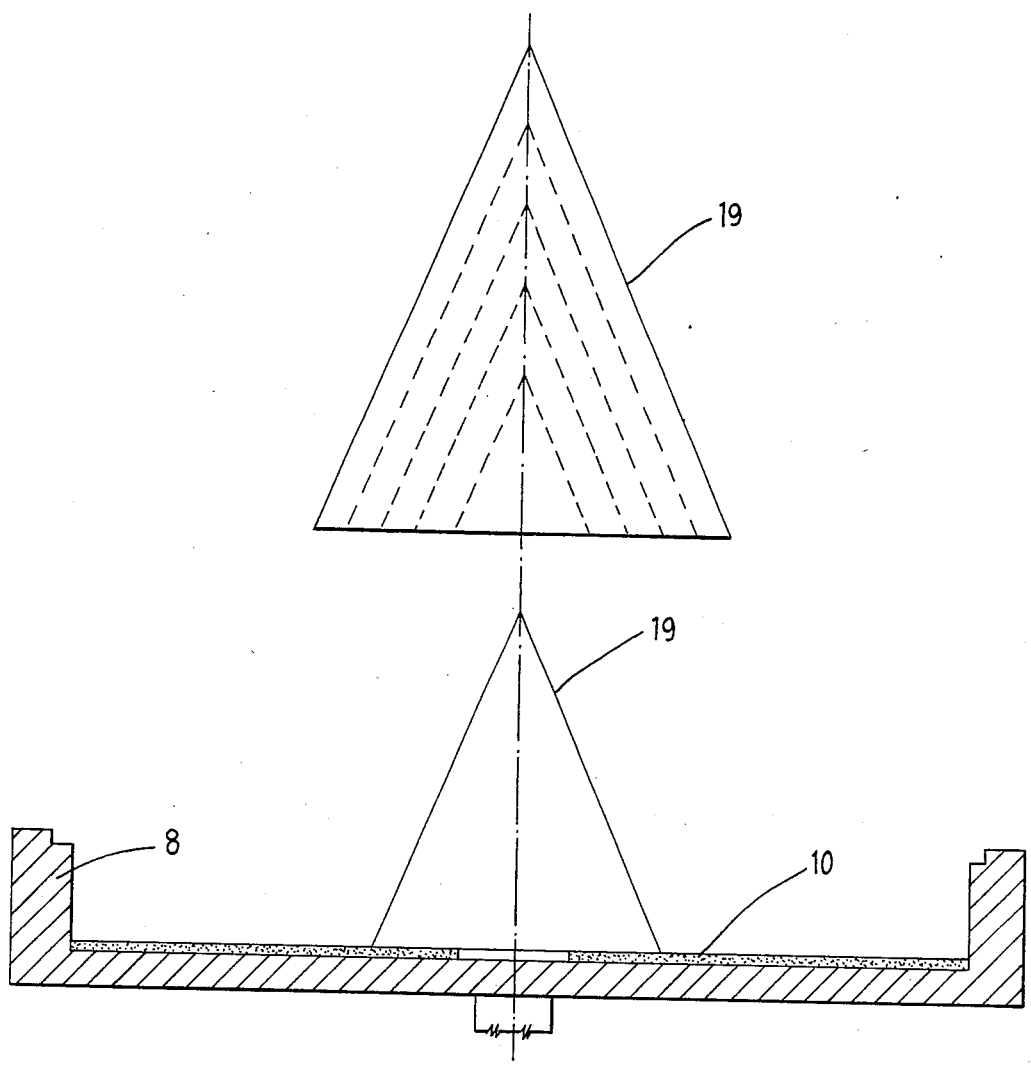
FIG. 2 is a fragmentary sectional side view showing the apparatus of FIG. 1 and removable conical flow medium applying elements which can be utilized in association therewith.

4. The circular unit for the addition of solvent (FIG. 2)

The selection of the place for the addition of a flow medium is given by the use of annular forms with different radius. A ring-shaped series of elements 19 is used, in which the smallest element has a radius larger than the radius of the plate 10 at the start of the layer; and the largest element of the ring-shaped series of elements 19 has a radius smaller than the radius of the plate 10 at the end of the layer. Said ring-shaped series of elements 19 can, for example, as shown in the upper part of FIG. 2, consist of cone-shaped shells 19 which can be placed one after another. The height of each cone has an influence on the speed of the addition of the flow medium and it must be chosen in dependence on the viscosity of the flow medium which is being used. The cones must consist of an inert material in which a constant flow medium speed is assured, for example chromatography paper.

DESCRIPTION OF THE METHOD

The sequential centrifugal stratification chromatography unit works in such a manner that a substance mixture which is to be separated is first applied near the centerpoint of the layer. A first chromatographic base separation can lead to:

(a) the creation of one or more outer zones of pure separated substances and one or more inner zones of mixed substances, or (b) the creation of one or more outer zones of mixed substances and one or more inner zones of separated substances.

The addition of the flow medium or mobile phase is stopped in case (a) after the base separation and the unit for the addition of flow medium I is adjusted so that the one or more zones of separated substances are eluted centrifugally accelerated from the outside to the inside one after the other with a strong elution medium (for example methanol, etc.). The addition of the flow medium is again stopped for the reprocessing of one or more inner mixed substance zones. The rotating, wet layer 10 is thereafter dried with an inert gas (for example nitrogen) at a suitable temperature. After the layer 10 has been dried, the rotation is stopped. Then, a circular element 19 (from the ring-shaped series of elements) for the addition of flow medium is placed onto the layer 10 and the remaining zone(s) are pushed back using a strong elution medium (for example methanol etc.) with the help of capillary force in direction of the centerpoint to the start of the layer, so that the remaining zone(s) is(are) concentrated and thus lead to a dissolution, which is better for the following separation process. (However, there exists also the possibility to use a specific eluent to further develop the remaining zone(s) in the direction of the centerpoint with the help of the capillary force.)

The fluid medium supply is finally stopped, the circular unit 19 for the addition of fluid medium is removed, and the layer 10, while the rotor is stationary, is dried in the aforedescribed manner. Then, the remaining zone which is concentrated or is anticircularly developed with the help of the capillary force is further separated. The addition of a flow medium occurs thereby again at the start of the layer 10. Thereafter, the aforedescribed procedure starts again, and can be repeated a sufficient number of times until the total separation has been solved satisfactorily.

In the case (b), the one or more outer mixed substance zone(s) is(are), after stopping the solvent supply and corresponding adjusting of the unit for the addition of solvent I, separated one after the other starting with the outermost zone using specific flow mediums. For the treatment of the remaining one or more inner mixed substance zone(s), the analog, afore-described procedure is to be selected. If the separation path is too short, the one or more mixed substance zone(s) can again be guided back to the inside of the chromatography plate 10 and can be subjected to another development with a suitable flow medium.

If one foregoes the circular unit for the addition of flow medium (II), there exists the possibility to work anticircularly in the first three apparatuses (I) at a low rotational speed, with this one can either push the not separated substances back in the direction of the addition zone or one can further separate the substances in this direction with a suitable flow medium.

Example of Application of the Sequential Centrifugal Chromatographic Stratification Chromatography A mixture of five furanocoumarines, 5-methoxy-2H-furo[2,3-h]-1-benzopyran-2-one (iso-bergapten), 5,6,-dimethoxy-2H-furo[2,3-h]-1-benzopyran-2-one pimpinellin), 4-methoxy-7H-furo [3,2-g]-1-benzopyran-7-one (bergapten), 4,9-dimethoxy-7H-furo[3,2-g]-1-benzopyran-7-one 2,3-h]-1- benzopyran-2-one (sphondin) in a total amount of 50 mg. was dissolved in 0.5 ml. chloroform and applied on the inside of the chromatography plate, which was coated with silica gel PF 254 (Merck). The layer radius was 10 cm, the rotor speed was constant: 750 rpm.

FIG. 6 shows the separation of the five furanocoumarines with the sequential centrifugal chromatographic stratification chromatography in four steps. During each partial step, the Figure illustrates on top the separation on the plate and thereunder the corresponding hypothetical densitogram, wherein B=bergapten, IP-=isopimpinellin, Sph=sphondin, IB=isobergapten, P=pimpinellin.

Figure 6A:
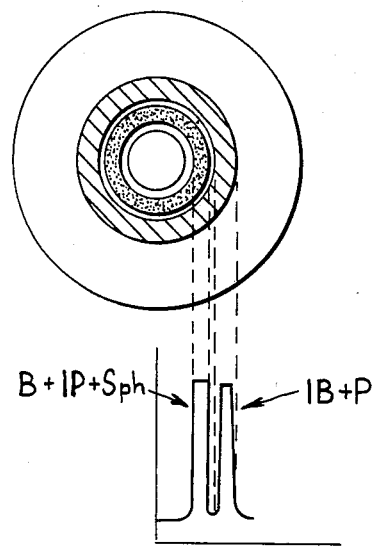
FIGS. 6a-6d are diagrams showing successive steps in the separation of components of a mixture according to the inventive method.
Figure 6B:
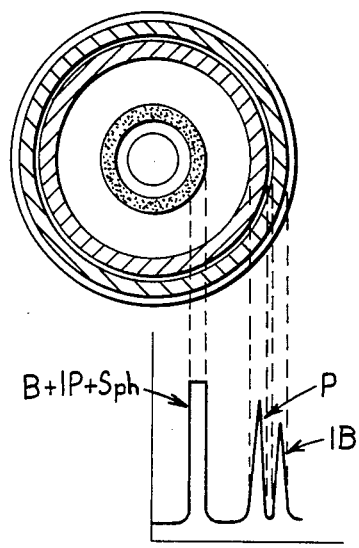
Figure 6C:
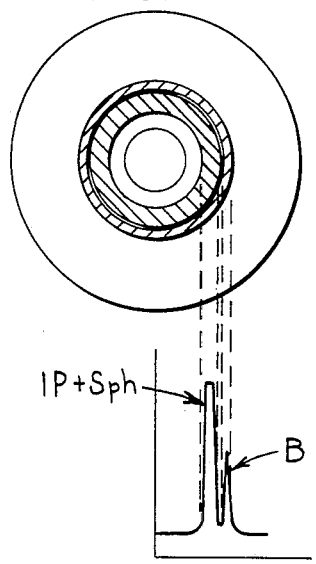

After the drying, in a first base separation using n-hexane-tetrahydrofuran (70:30) as flow medium, isobergapten and pimpinellin (zone 1), and bergapten, iso-pimpinellin and sphondin (zone 2) were separated (FIG. 6a). The separation was stopped, the adsorbent was dried and with the swingable unit for the addition of a flow medium, the mobile phase n-hexane-chloroform-tetrahydrofuran (64:16:1) was added between both zones 1 and 2. Chromatography took place until the complete separation of iso-bergapten and pimpinellin (FIG. 6b). Then, the flow medium supply was stopped, the layer was dried and the two substances with the help of the swivel arm were eluted with methanol one after the other quickly and in small volumes from the layer. The substances of the inner zone remain stationary during this step. After a renewed drying of the plate, again starting near the centerpoint, chromatography took place with n-hexane-chloroformtetrahydrofuran (64:16:1) as the flow medium, until bergapten was recognized as a zone clearly separate from iso-pimpinellin and sphondin (FIG. 6c). The flow medium supply was again stopped and the bergapten zone was eluted quickly and in a small volume after an inbetween drying with methanol.

Drying took place again thereafter. The remaining substances were separated with methylenechloride 100%, wherein the addition of flow medium occurred again near the centerpoint.

Figure 6D:
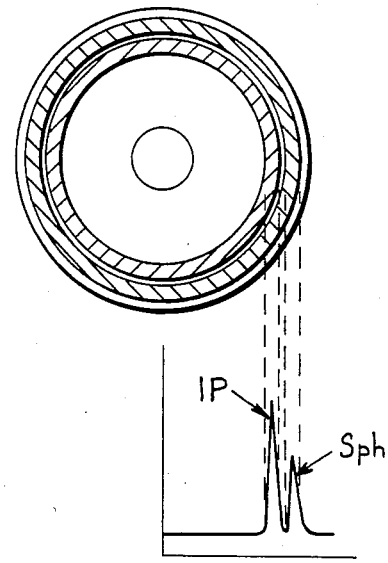

In order to have a separation path which is sufficiently large for the separation of the still remaining substances, the rotation was stopped, a fitting cone of a special filter paper was applied, and the zone was pushed back with methanol in the direction of the centerpoint to near the start of the layer. After an inbetween drying, iso-pimpinellin and sphondin were finally separated with methylenechloride 100% until a clear zone separation occurred (FIG. 6d). After the inbetween drying, both substances were one after the other quickly and in small volumes washed out of the layer by using methanol.

Publications which were filed after the Swiss patent application in this technique (1) Sz. Nyiredy, C. A. J. Erdelmeier and 0. Sticher, Farm. Tijdschr. Belg. 61 (1984) 262.
(2) Sz. Nyiredy, C. A. J. Erdelmeier and 0. Sticher, HRC & CC 8 (2), (1985) 73.
(3) C. A. J. Erdelmeier, Sz. Nyiredy and 0. Sticher, HRC & CC 8 (3), (1985) 132.
(4) Sz. Nyiredy, C. A. J. Erdelmeier and 0. Sticher, Instrumental Preparative Planor Chromatography in "Planor Chromatography" (Ed. R. E. Kaiser et al), Dr. A. Huethig Verlag, Heidelberg—New York—Basel (in press).

The embodiments of the invention in which an exclusive property or privilege is claimed are defined as follows:

1. A method for separating complonents of a mixture by a sequential centrifugal stratification chromatographic technique utilizing a rotatably supported rotor which includes an adsorbing medium, comprising the steps of:
    (a) applying the mixture which is to be separated to a radially inner part of said adsorbing medium on said rotatable rotor;
    (b) separating the mixture by rotating said rotor and by applying to a radially inner part of said adsorbing medium on said rotating rotor a first eluent which effects different amounts of radially outward migration of the components of the mixture through said adsorbing medium on said rotor through the action of centrifugal force;
    (c) thereafter stopping said migration of the components of the mixture;
    (d) thereafter applying a second eluent to a circular region of said adsorbing medium which is concentric to the axis of rotation of said rotor and which has a radius within a range bounded by said radially inner part and a radially outer edge portion of said adsorbing medium, said second eluent causing at least one of the components of the mixture which is near said circular region of said adsorbing medium to migrate radially through said adsorbing medium through capillary action;
    (e) thereafter interrupting the application of eluent to said adsorbing medium;
    (f) thereafter drying said adsorbing medium;
    (g) thereafter rotating said rotor and applying a third eluent to a circular region of said adsorbing medium which is concentric to the axis of rotation of said rotor, said third eluent causing at least one of the components of the mixture to migrate radially outwardly through said adsorbing medium through the action of centrifugal force and to be eluted from a radially outer edge of said adsorbing medium; and
    (h) collecting and discharging each component which is eluted from said radially outer edge of said adsorbing medium on said rotating rotor.

2. The method of claim 1, including the step of repeating steps (e) through (h) at least once.

3. The method of claim 1, wherein said circular region to which said third eluent is applied is spaced a substantial radial distance from said radially inner part of said adsorbing medium.

4. The method of claim 1, wherein said step of stopping said migration includes the step of substantially reducing the rotational speed of said rotor during said step of applying said second eluent to said adsorbing medium.

5. The method of claim 1, wherein said step of stopping said migration includes the step of stopping said rotor during said step of applying said second eluent to said adsorbing medium.

6. The method of claim 1, wherein said step of stopping said migration includes the step of stopping the addition of said first eluent to said adsorbing medium.

7. The method of claim 1, wherein each component of the mixture which migrates radially in response to the application of said second eluent is migrating in a radially inward direction.

8. The method of claim 1, wherein each component of the mixture which migrates radially in response to application of the second eluent is migrating in a radially outward direction.

9. The method of claim 1, wherein said first eluent, said second eluent and said third eluent are different from each other.

10. The method of claim 1, wherein at least two of said first, second and third eluents are identical.

11. A method for separating components of a mixture utilizing a layer of an adsorbing material which is supported for rotation about an axis extending perpendicular to said layer, comprising the steps of: applying a quantity of the mixture to a radially inner portion of said adsorbing medium; rotating said adsorbing medium at a first speed and simultaneously applying a first eluent to said radially inner portion of said adsorbing medium, whereby said first eluent and centrifugal force effect radially outward movement of respective components of said mixture at different speeds until each of a plurality of said components is disposed within a respective one of a plurality of concentric and radially spaced circular regions of said adsorbing medium; thereafter applying a second eluent to a further circular region of said adsorbing medium which is concentric with respect to said first-mentioned circular regions, and which is spaced radially outwardly from said radially inner portion and is radially between two adjacent said first-mentioned circular regions.

12. The method of claim 11, including the step of determining whether any said first mentioned circular region includes more than one component of said mixture and, following a determination that one of said first mentioned circular regions includes two components of the mixture, the steps of reducing the speed of rotation of said adsorbing medium to a value within a range bounded by zero and a second speed substantially slower than said first speed, and then applying to a circular region of said adsorbing medium adjacent and concentric to said one of said first-mentioned circular regions an eluent which effects radial migration through capillary action of at least one of the components of the mixture in said one of said first-mentioned circular regions.

* * * * *